US009652585B2

(12) United States Patent
Craig et al.

(10) Patent No.: US 9,652,585 B2
(45) Date of Patent: May 16, 2017

(54) COMPARATIVE GENOMIC HYBRIDIZATION ARRAY METHOD FOR PREIMPLANTATION GENETIC SCREENING

(75) Inventors: Andrew Craig, Letchworth Garden (GB); Anthony Brown, Cambridge (GB); Nicholas Haan, Cambridge (GB)

(73) Assignee: BLUEGNOME LIMITED, Cambridge (GB)

( * ) Notice: Subject to any disclaimer, the term of this patent is extended or adjusted under 35 U.S.C. 154(b) by 529 days.

(21) Appl. No.: 12/724,865

(22) Filed: Mar. 16, 2010

(65) Prior Publication Data

US 2011/0230362 A1 Sep. 22, 2011

(51) Int. Cl.
| | |
|---|---|
| C12M 1/34 | (2006.01) |
| C12M 3/00 | (2006.01) |
| C12Q 1/68 | (2006.01) |
| C12P 19/34 | (2006.01) |
| G01N 33/00 | (2006.01) |
| C07H 21/02 | (2006.01) |
| C07H 21/04 | (2006.01) |
| G06F 19/20 | (2011.01) |
| G06F 19/18 | (2011.01) |

(52) U.S. Cl.
CPC ........... *G06F 19/20* (2013.01); *C12Q 1/6827* (2013.01); *G06F 19/18* (2013.01)

(58) Field of Classification Search
USPC .............. 435/6.1, 611, 6.12, 183, 91.1, 91.2, 435/283.1, 287.1, 287.2; 436/94, 501; 536/23.1, 24.3, 24.33, 25.3
See application file for complete search history.

(56) References Cited

U.S. PATENT DOCUMENTS

| | | | | |
|---|---|---|---|---|
| 5,665,572 | A * | 9/1997 | Ikeda et al. ................. | 435/91.2 |
| 7,371,516 | B1 * | 5/2008 | Burchard ..................... | 435/6.12 |
| 2003/0165895 | A1 * | 9/2003 | Czerniak et al. ............ | 435/6 |
| 2005/0014147 | A1 | 1/2005 | Hessner | |
| 2005/0014184 | A1 * | 1/2005 | Shah .............................. | 435/6 |
| 2005/0032060 | A1 * | 2/2005 | Shah et al. ................... | 435/6 |
| 2005/0239104 | A1 | 10/2005 | Ferea et al. | |
| 2007/0111233 | A1 * | 5/2007 | Bianchi et al. .............. | 435/6 |
| 2007/0238121 | A1 * | 10/2007 | Ballif et al. ................. | 435/6 |
| 2008/0274909 | A1 | 11/2008 | Brothman | |
| 2009/0104613 | A1 * | 4/2009 | Adler ........................... | 435/6 |
| 2009/0176226 | A1 | 7/2009 | Wu et al. | |

FOREIGN PATENT DOCUMENTS

| | | |
|---|---|---|
| WO | 2005/028674 A2 | 3/2005 |
| WO | 2005/044086 A2 | 5/2005 |
| WO | 2006/023769 A2 | 3/2006 |
| WO | 2007/022530 A2 | 2/2007 |

OTHER PUBLICATIONS

Hu et al., Aneuploidy detection in single cells using DNA array-based comparative genomic hybridization. Molecular Human Reproduction, 10, 283-289, 2004.*

Nigel P. Carter, Methods and strategies for analyzing copy number variation using DNA microarrays, Nat. Genet. Jul. 2007; 39 (7 Suppl); S16-S21 (11 pages).
Kwong-Kwok Wong et al., Allelic imbalance analysis by high-density single-nucleotide polymorphic allele (SNP) array with whole genome amplified DNA, Nucleic Acids Research, 2004, vol. 32, No. 9, pp. 1-8.
Jonathan R. Pollack et al., Microarray analysis reveals a major direct role of DNA copy number alteration in the transcriptional program of human breast tumors, PNAS, Oct. 1, 2002, vol. 99, No. 20, pp. 12963-12968.
Notification of Transmittal of The International Search Report and the Written Opinion of the International Searching Authority, or the Declaration, Form PCT/ISA/220, dated Dec. 15, 2011, from PCT/IB2011/000438.
International Search Report, Form PCT/ISA/210, dated Dec. 15, 2011, transmitted with Form PCT/ISA/220, 3 pages, from PCT/IB2011/000438.
Written Opinion of the International Searching Authority, Form PCT/ISA/237, dated Dec. 15, 2011, transmitted with Form PCT/ISA/220, 4 pages, from PCT/IB2011/000438.
Donna G. Albertson, et al., "Genomic Microarrays in Human Genetic Disease and Cancer," Human Molecular Genetics, 2003, vol. 12, Review Issue 2, Oxford Press University, Oxford, UK, pp. R145-R152.
Tineke E. Buffart, et al., "Across Array Comparative Genomic Hybridization: A Strategy to Reduce Reference Channel Hybridizations," Genes, Chromosomes & Cancer, 2008, 47:994-1004, Wiley-Lizz, Inc., Amsterdam, The Netherlands.
Dong Gui Hu, et al., "Aneuploidy Detection in Single Cells Using DNA Array-Based Comparative Genomic Hybridization," Molecular Human Reproduction, 2004, vol. 10, No. 4, pp. 283-289, Oxford Press University, Oxford, UK.
Thomas Laframboise, "Single Nucleotide Polymorphism Arrays: A Decade of Biological, Computational and Technological Advances," Nucleic Acids Research, 2009, vol. 37, No. 13, pp. 4181-4193, Cleveland, Ohio.
Antonie M. Snijders, et al., "Current Status and Future Prospects of Array-Based Comparitive Genomic Hybridization," Briefings in Functional Genomics and Proteomics, Apr. 2003, vol. 2, No. 1, pp. 37-45, Henry Stewart Publications, San Francisco, CA.
Dagan Wells, et al., "Comprehensive Chromosomal Analysis of Human Preimplantation Embryos Using Whole Genome Amplification and Single Cell Comparative Genomic Hybridization," Molecular Human Reproduction, 2000, vol. 6, No. 11, pp. 1055-1062, Oxford Press University, Oxford, UK.

(Continued)

*Primary Examiner* — Frank Lu
(74) *Attorney, Agent, or Firm* — Mueting, Raasch & Gebhardt, P.A.

(57) ABSTRACT

A method for determining the presence of a copy number imbalance in genomic DNA of a test sample is provided. The method can separately measure hybridization of a single test sample to a first hybridization array and hybridization of a plurality of reference samples to a plurality of other, respective test arrays. A determination of copy number can be based on the best fit reference array, relative to the test array. The best fit can be determined based on the closest or most similar signal-to-noise ratio of the measured signals.

23 Claims, 5 Drawing Sheets

(56) References Cited

OTHER PUBLICATIONS

Dagan Wells, et al., "Use of Comprehensive Chromosomal Screening for Embryo Assessment: Microarrays and CGH," Molecular Human Reproduction, 2008, vol. 14, No. 12, pp. 703-710, Oxford Press University, Oxford, UK.
Notification Concerning Transmittal of International Preliminary Report on Patentability, Form PCT/IB/326, dated Sep. 27, 2012, from PCT/IB2011/000438.
International Preliminary Report on Patentability, Form PCT/IB/373, dated Sep. 18, 2012, 5 pages, transmitted with Form PCT/IB/326 on Sep. 27, 2012, from PCT/IB2011/000438.
Office Action from SIPO, dated Apr. 22, 2014, for Chinese Patent Application No. 201180024202.4, with English-language translation.
Office Action from JPO, dated Jun. 25, 2014, for Japanese Patent Application No. JP2012-557617, with English-language translation.
Notice of Acceptance from IP Australia, dated Jun. 4, 2014, for Australian Patent Application No. 2011228794.
Ryusuke Mamada et al. "Gene diagnostic method of ovum cells not using nuclei of fertilized ova", Proceedings of annual meeting of the Society of Chemical Engineers, Japan, 1990, vol. 55, p. 275. Described in Japanese Office Action at pp. 5-6 of the translation.
Buffart et al. "DNA copy number profiles of gastric cancer precursor lesions," BioMed Central Ltd., BMC Genomics, Oct. 2007, 8:345.
Buffart et al. "Across Array Comparative Genomic Hybridization: A Strategy to Reduce Reference Channel Hybridizations," Genes, Chromosomes & Cancer, 2008, vol. 47 (pp. 994-1004).
Le Caignec et al. "Single-cell chromosomal imbalances detection by array CGH," Nucleic Acids Research, May 12, 2006, vol. 34, No. 9, e68, (pp. 1-12), Oxford University Press.

\* cited by examiner

COMPARATIVE GENOMIC HYBRIDIZATION ARRAY METHOD FOR PREIMPLANTATION GENETIC SCREENING

FIELD

The present teachings relates to methods for detecting genetic abnormalities within the cells of an embryo, oocyte, polar body, or associated biopsy.

BACKGROUND

Within the field of IVF (in-vitro fertilization) it is desirable to identify the number and complement of chromosomes within the cells of an embryo prior to implantation. There is increasing evidence that one of the most important factors influencing embryo viability is chromosome imbalance, including copy number gain/loss and whole chromosome aneuploidy (abnormal number of chromosomes).

Current methods for testing first involve isolation of the genetic material which is representative of the embryo for testing. Samples currently used in the analysis of aneuploidy are a polar body biopsy associated with the oocyte, a single cell from blastomere biopsy (associated with the day 3 embryo), or trophoectoderm biopsy (associated with the day 5 embryo, or blastocyst). In some cases, however, samples taken at other or multiple points in the process prove more effective. The polar body or cell(s) are then tested via a choice of methods to detect copy number imbalance. For the purposes of the present application, such testing methods will be referred to as preimplantation genetic screening (PGS), although the term PGD is often encountered in the literature. The term PGS shall also include testing of polar bodies to access oocyte quality, for example, to enable informed egg banking.

Comparative genomic hybridization (CGH) is a technique that has been employed to detect the presence and identify the location of amplified or deleted sequences in genomic DNA, corresponding to so-called changes in copy number. Typically, genomic DNA is isolated from normal reference cells, as well as from test cells. The two nucleic acid samples are differentially labeled and then hybridized in-situ to metaphase chromosomes of a reference cell. The repetitive sequences in both the reference and test DNAs are either removed or their hybridization capacity is reduced by some means. Chromosomal regions in the test cells which are at increased or decreased copy number can be identified by detecting regions where the ratio of signal from the two DNAs is altered. The detection of such regions of copy number change can be of particular importance in the diagnosis of genetic disorders.

Metaphase CGH, as described above, has also been applied to and has the ability to screen all chromosomes for abnormalities. For CGH analysis to be applied to a PGS context, amplification of the entire genome is required to increase the quantity of DNA from a single cell (5-10 pg) to levels suitable for metaphase CGH (1 µg) prior to analysis. Commonly used methods for amplification include DOP-PCR (Telenius et al., 1992) or more recently whole-genome amplification kits such as, GENOMEPLEX (Rubicon genomics) and REPLI-G (Qiagen). The main problem with using metaphase CGH in a clinical setting is that it can take around 4 days to complete, which is not compatible with the time frame required for the pre-implantation of embryos in IVF, without the freezing of embryos and implantation occurring in the following cycle. In addition, the method is technically challenging and requires high levels of expertise to carry out and analyze. These difficulties have limited the widespread use of metaphase CGH in PGS.

Pinkel et al. in 1998 and 2003 disclosed the technique which has become more widely known as array comparative genomic hybridization, hereafter referred to as arrayCGH. In 1998, Solinas-Toldo et al. described a similar "Matrix-based comparative genomic hybridization" approach.

The arrayCGH technique relies on similar assay principles to CGH with regard to exploiting the binding specificity of double stranded DNA. In arrayCGH, the metaphase chromosomes of a reference cell are replaced with a collection of potentially thousands of solid-support-bound unlabelled target nucleic acids (probes), for example, an array of clones which have been mapped to chromosomal locations. ArrayCGH is thus a class of comparative techniques for the high throughput detection of differences in copy number between two DNA samples, both of which are hybridized to the same hybridization area. It has advantages over CGH in that it allows greater resolution to be achieved and has application to the detection and diagnosis of genetic disorders induced by a change in copy number, in addition to other areas where copy number detection is important. While the particulars vary, a range of different probe types can be used, including those encountered in oligonucleotide, PAC, and bacterial artificial chromosomes (BAC) arrays.

ArrayCGH is currently being used to support the efforts of clinicians in the investigation of genomic imbalance in constitutional cytogenetics and increasingly in oncology. These applications are incredibly demanding such that the microarrays designed for these applications must be produced to far more rigorous standards than those used in academic or pre-clinical research applications.

ArrayCGH has an advantage over metaphase CGH in that the interpretation is much simpler and easily automated; in addition the time taken for the complete analysis is shorter. ArrayCGH can be used to detect aneuploidy in single cells and has been successfully applied to PGS. Single cells have to be amplified for the technique and the same methods are employed as those used in metaphase CGH. ArrayCGH allows comprehensive analysis of the whole genome to be completed within 48 hours, which allows aneuploidy screening without cryopreservation in PGS.

In order to achieve optimal assay results, arrayCGH requires the test and reference samples to be well matched in terms of quality and concentration. In the context of PGS, the starting point for any analysis is the genetic material which is as representative as possible of the fertilized embryo, or oocyte in the context of egg banking. Currently it is possible to examine the genetic material contained within a polar body or a blastomere, a single cell extracted from an 8 cell embryo, or alternatively a small number of cells from a blastocyst or associated biopsy. As only a limited amount of DNA can be obtained from such material, most downstream analyses require DNA amplification procedures to be used in order to produce large numbers of copies of the starting material. It is to be understood that polar bodies are ejected as a fertilization process begins and there are two of them, PB1 and PB2. The process is not straight forward. Herein, the term "polar body" can comprise a body ejected or biopsied from a primary or secondary oocyte.

While un-amplified genomic reference material may be used, corresponding arrayCGH results can show high noise levels due to poor matching of amplified test with un-amplified reference. Thus, reference material used in this context is often a 'normal' pooled DNA sample diluted to contain a broadly similar quantity of DNA as a small number of single cells. This diluted reference material is then amplified using the same method as the test sample. Even though these steps are taken to match the properties of the test and reference samples this is not always effective and the clarity of results can vary. This may be for a wide variety of reasons, including: minor errors in the quantification of the starting DNA and hence variable quantities of DNA in the diluted sample; variation due to the stochastic nature of the amplification process; amplification of impurities in the sample which are not present in the reference; low sample DNA "quality" leading to increased non-specific amplification; variability in the quantity and type of reagents used in the extraction and storage of samples. In all cases, the resultant differences between amplification of sample and reference can both alter and obscure the results of the true amplification, leading to altered arrayCGH profiles, and frequently increased noise and suppressed dynamic range.

PGS is a diagnostic application, and it is standard practice for each experiment to include an internal control to demonstrate successful functioning of the experiment, and also to assess variation in dynamic range between experiments which, for example, may arise due to the amplification issues described previously. When using arrayCGH, the most commonly used approach to address this problem is to use a reference sample with known copy number gains/losses relative to the test sample. These can then be used as a measure of performance for each individual assay.

Most frequently, the reference sample is sex-mismatched against the test, giving a shift on the $\log_2$ ratio of test over reference for the X and Y chromosomes, and consequently a measure of dynamic range. While applicable in many contexts, in the case of PGS, however, it is generally not possible to know a priori the sex of the sample, especially in aneuploidy screening of blastomere or blastocyst biopsy samples that could be either sex. The use of a single reference as internal control is therefore not reliably possible. Moreover, selection of a single appropriate reference, with a known copy number imbalance in regions other than the sex chromosomes, to a test sample is generally not possible, as the degree of copy number variation in embryos/oocytes is extremely high, and current research indicates that there are no regions which are predictably stable. In some embodiments, the selection of an embryo for implantation can be made on the basis of aneuploidy status. In other embodiments, selection is made on the basis of smaller genetic aberrations.

An alternative is to use a reference which includes non-human control sequences. However, this approach is less than ideal as it is difficult to choose non-human sequences which accurately mimic the behavior of human sequences. In any case, the use of non-human control sequences can suffer from the same amplification biases, and other biases, and as such choice of a single reference can be challenging.

To overcome this problem in PGS, it would be necessary to carry out two conventional arrayCGH hybridizations to analyze a single test sample, one against a male and another against a female reference to ensure that the assay is working correctly. However, the cost associated with this approach is unacceptably high for the application.

Where two or more cells are taken from an embryo, for example, from a blastocyst/trophoectoderm), the possibility of mosaicism in the test sample becomes significant in a PGS context, as embryos are frequently mosaic. To complicate matters, the number of cells taken From the embryo may be unknown due to inaccuracy of biopsy methods. While arrayCGH can detect mosaicism, it provides no means to directly quantify this mosaicism due to a lack of sufficiently sophisticated internal controls and furthermore, for the same reason, may mistake experimental noise for mosaicism. ArrayCGH's reliance on a single reference sample is again problematic in this context.

ArrayCGH requires contrasting fluorescent dyes to label the test and reference samples. The popular dye pair Cy3 and Cy5 is often used for arrayCGH. The Cy5 dye is susceptible to degradation by ozone in the environment and particularly when combined with high humidity, this influence on assay quality can lead to the loss of experimental data. ArrayCGH is used wherein two fluorescently labeled samples are competitively hybridized to the same hybridization area, such that through ratiometric comparison relative gain or loss of genetic material can be ascertained. Typically, one sample is a test sample of unknown genetic make-up and one sample is a reference sample known to have normal copy number, where normality is defined by the application in question. ArrayCGH is a powerful and robust technique, however the PGS application presents unique technical challenges. In some embodiments, the assessment of chromosomal content of an embryo, can be made either directly through taking cells after fertilization, or indirectly through assessing polar bodies and thus the oocyte generating the embryo. In some embodiments, an application exists whose only purpose is to assess the content of the oocyte, and no embryo is necessarily generated. This is referred to herein as egg banking.

Buffart et al. (2008) suggest a modified arrayCGH technique that they term "across arrayCGH" (aaCGH), as an improvement to the current technologies. AaCGH is similar to arrayCGH, but instead of hybridization of the test and reference sample to a single hybridization area, test and reference samples are compared from separate hybridization areas. This method, independently developed by the authors of this patent, offers advantages in cost and potentially in data quality as it removes any noise due to dye bias. The quality of the profiles obtained using aaCGH were reported to match or even surpass those obtained using regular dual channel arrayCGH. The reference is described as being hybridized at the same time, on the same slide, as the test using a multi format array, and the test and reference are labeled with the same fluorescent dye. They compare a single test sample with a single reference sample. The method does not, however, overcome the unique challenges of PGS.

SNP array techniques, as distinct from arrayCGH, may also be used to determine copy number in DNA samples, and have also been deployed for PGS applications. SNP arrays over screening of all chromosomes and allow concurrent genotyping. The mechanism used is substantially different than the arrayCGH mechanism in that the technique is not comparative. No reference sample is used and no co-hybridization is performed, and the method for copy number assignment relies on quantification of individual alleles and subsequent ratiometric analysis in contrast to arrayCGH where individual alleles are not assessed. Disadvantages of SNP arrays include increased noise levels, longer protocols, complexity of data interpretation and ethical implications, and possibly lower applicability to haploid samples.

The molecular cytogenetic technique of FISH (fluorescence in-situ hybridization), which uses chromosome-specific DNA probes, has frequently been applied to PGS and gives detectable signals on interphase nuclei. Although no amplification step is required, a significant disadvantage exists is that only a limited number of chromosomes can be assessed concurrently, limited by the number of distinct colors available for labeling of the DNA probes. The most comprehensive FISH methods used for routine embryo screening currently assess only half of the chromosomes, and thus, some chromosomal abnormalities are missed. Other disadvantages of FISH include overlapping signals which are difficult to score.

SUMMARY

A feature of the present teachings is to provide a method for determining the presence of a copy number imbalance in genomic DNA of a test DNA sample that reduces the risk of assay failure due to poor matching of test and reference samples associated with conventional arrayCGH. This method can increase assay quality, accuracy, and yield.

Another feature of the present teachings is provide a method for determining the presence of a copy number imbalance in genomic DNA of a test DNA sample that separately measures hybridization of a single test sample to one hybridization array and hybridization of a set of reference samples to one or more other hybridization arrays.

An additional feature of the present teachings is to provide a method for determining the presence of a copy number imbalance in genomic DNA that comprises selection of a single optimal pairing of test DNA and reference DNA samples.

The present teachings provide a method for determining the presence of a copy number imbalance in genomic DNA of a test sample. The sample can comprise labeling sample genomic DNA from a test sample, or an amplification product thereof, to form labeled test DNA, hybridizing the labeled test DNA to a first hybridization array, labeling first reference genomic DNA from a reference sample, or an amplification product thereof, to form labeled first reference DNA, hybridizing the labeled first reference DNA to a second hybridization array, labeling second reference genomic DNA from a second reference sample, or an amplification product thereof, to form labeled second reference DNA, and hybridizing the labeled second reference DNA to a third hybridization array. The method can comprise analyzing the first hybridization array after the hybridizing of the labeled test DNA to determine signal intensities produced by hybridization of the labeled test DNA, analyzing the second hybridization array after the hybridizing of the labeled first reference DNA to determine signal intensities produced by hybridization of the labeled first reference DNA, and analyzing the third hybridization array after the hybridizing of the labeled second reference DNA to determine signal intensities produced by hybridization of the labeled second reference DNA.

The present teachings provide a method for estimating a copy number for at least one region of a sample genomic DNA by comparing the signal intensities of a test hybridization array with the signal intensity of at least one of two or more reference hybridization arrays.

Additional features and advantages of the present teachings will be set forth in part in the description that follows, and in part will be apparent from the description, or may be learned by practice of the present teachings. The objectives and other advantages of the present teachings will be realized and attained by means of the elements and combinations particularly pointed out in the description and appended claims.

It is to be understood that both the foregoing general description and the following detailed description are exemplary and explanatory only and are intended to provide a further explanation of the present teachings, as claimed.

BRIEF DESCRIPTION OF DRAWINGS

The accompanying drawings, which are incorporated in and constitute a part of this application, illustrate some of the embodiments of the present teachings and together with the description, serve to explain the principles of the present teachings.

DETAILED DESCRIPTION

Figure 1:
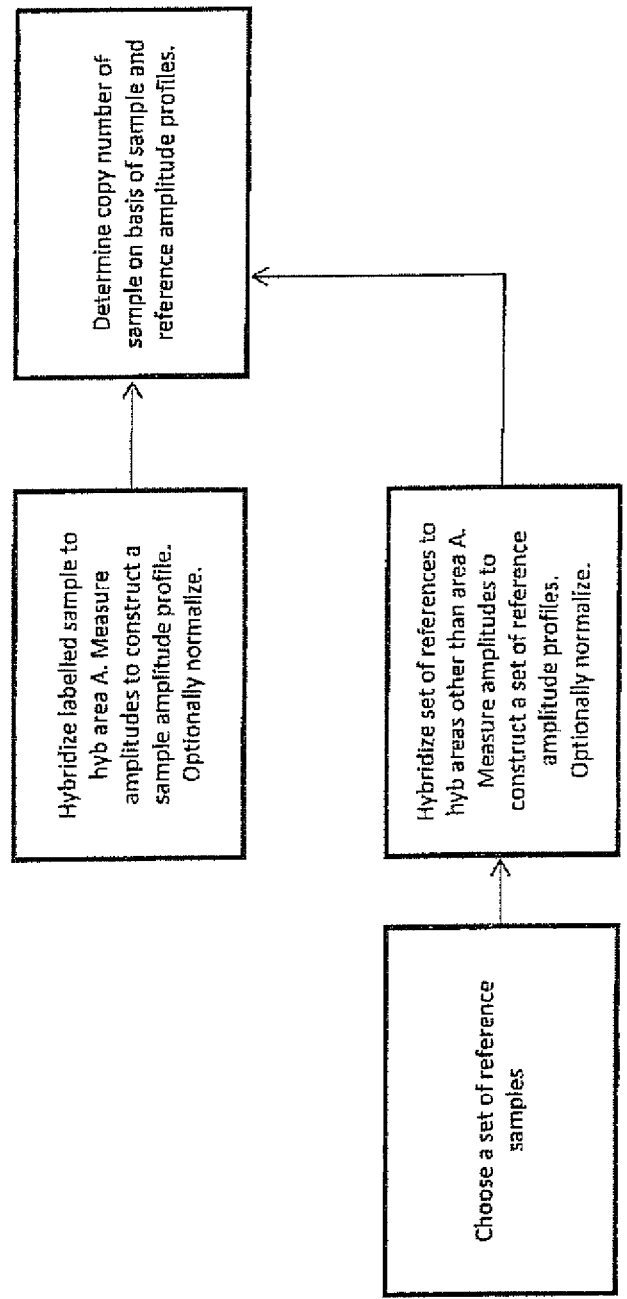
FIG. 1 is a flowchart depicting an exemplary method for determining copy number of a test DNA sample, according to the present teachings.

The present teachings relate to a method for detecting aneuploidy, or the presence of smaller copy number imbalances or smaller imbalances in genomic DNA. The method for detecting aneuploidy or detection of copy number imbalance ("the detection method") according to the present teachings can be useful in analyzing an oocyte prior to egg banking or can be useful in pre-implantation genetic screening (PGS) to identify the number and complement of chromosomes within the cells of an embryo prior to implantation using in-vitro fertilization procedures. The detection method can identify chromosomal regions in genomic DNA that is representative of the embryo for testing ("test DNA"), which contain an increased or decreased copy number. The detection method can comprise using single channel array comparative genomic hybridization ("single channel array-CGH"), whereby a test DNA is hybridized to a hybridization array, and one or more DNA molecules for which the copy number is already known ("reference DNA") is hybridized to one or more different hybridization arrays. A copy number imbalance in the test DNA can be identified by detecting regions where the signal intensities resulting from hybridization of the reference DNA and hybridization of the test DNA, are different. Various features of the present teachings can include the genomic hybridization methods, devices, and kits described in WO 96/17958 and in U.S. patent application Ser. No. 12/609,156, filed Oct. 30, 2009, the contents of which are incorporated by reference herein in their entireties.

The detection method can comprise labeling a test sample DNA obtained from a test sample to form a test DNA and hybridizing the labeled test DNA to a first hybridization array. The test sample DNA can be labeled to permit detection and/or measurement of hybridization of the test sample DNA to the first hybridization array. The signals generated by hybridization of the labeled test DNA can be detected and analyzed to determine signal intensity produced from the first hybridization array, and thereby obtain test hybridization results. The test hybridization results can be compared to reference hybridization results, or signal intensity generated by hybridization of one or more reference DNA to one or more other hybridization arrays that are separate from the first hybridization array. For example, the signal intensity for a reference DNA can be determined by labeling a reference DNA and hybridizing the labeled reference DNA to a second hybridization array. The signals generated by hybridization of the labeled reference DNA can be detected and analyzed to determine the signal intensity of the reference DNA. The presence of a copy number imbalance in the test DNA can be determined by identifying one or more regions of the first hybridization array where the signal intensity differs from the signal intensity produced in one or more corresponding regions of the second hybridization array.

The determination of a signal intensity produced by hybridization of the labeled reference DNA can occur prior to or after the determination of a signal intensity produced by hybridization of the labeled test DNA. If the determination of a signal intensity produced by hybridization of the labeled reference DNA occurs prior to the determination of signal intensity produced by hybridization of the labeled test DNA, the reference hybridization results can be recorded and stored as historical reference hybridization results. Test hybridization results which are later obtained for a test sample DNA can then be compared to the historical reference hybridization results to determine a copy number imbalance in the test DNA. Use of historical reference hybridization results can avoid the need to perform actual hybridizations for a reference sample each time comparison with particular test hybridization results is desired.

More than one reference DNA or a plurality of reference DNA samples can be used in the detection method. For example, after determining the signal intensity of the reference DNA, the signal intensity for a second reference DNA can be determined. The signal intensity for the second reference DNA can be determined by labeling and hybridizing the second reference DNA to a third hybridization array. The signals generated by hybridization of the labeled second reference DNA can be detected and analyzed to determine the signal intensity produced by hybridization of the second reference DNA. The presence of a copy number imbalance can be determined by identifying one or more regions of the first hybridization array where the signal intensity differs from the signal intensity produced in one or more corresponding regions of the second and/or third hybridization array.

The method for determining the presence of a copy number imbalance in genomic DNA of a test sample can comprise labeling sample genomic DNA from a test sample, or an amplification product thereof, to form labeled test DNA, hybridizing the labeled test DNA to a first hybridization array, labeling first reference genomic DNA from a reference sample, or an amplification product thereof, to form labeled first reference DNA, hybridizing the labeled first reference DNA to a second hybridization array, labeling second reference genomic DNA from a second reference sample, or an amplification product thereof, to form labeled second reference DNA, and hybridizing the labeled second reference DNA to a third hybridization array. The method can comprise analyzing the first hybridization array after the hybridizing of the labeled test DNA to determine a signal intensity produced by hybridization of the labeled test DNA, analyzing the second hybridization array after the hybridizing of the labeled first reference DNA to determine a signal intensity produced by hybridization of the labeled first reference DNA, and analyzing the third hybridization array after the hybridizing of the labeled second reference DNA to determine a signal intensity produced by hybridization of the labeled second reference DNA. A copy number can be estimated for at least one region of the sample genomic DNA by comparing the signal intensities of the first hybridization array with the signal intensity of at least one of the second hybridization array and the third hybridization array.

The labeled first reference DNA can include at least one copy number change in one or more pre-defined regions of the genome, relative to the labeled test DNA. The labeled second reference DNA can include at least one pre-defined region which does not have the same copy number change relative to the labeled test DNA, as the labeled first reference DNA does. In some cases, the signal intensity produced by hybridization of the labeled test DNA is compared to the signal intensity produced by hybridization of the labeled first reference DNA in the one or more pre-defined regions, the signal intensity produced by hybridization of the labeled test DNA is compared to the signal intensity produced by hybridization of the labeled second reference DNA in the one or more pre-defined regions, and the method further comprises determining a dynamic range of the method based on an expected copy number. The labeled first reference DNA can be from a male animal of a first species, for example, a mammal such as a human, and the labeled second reference DNA can be from a female animal of the first species. The labeled first reference DNA and the labeled second reference DNA can comprise a mixture of DNA from a male and from a female of a same species of animal. The labeled first reference DNA can include a trisomy and the second reference DNA can include a monosomy. In some embodiments, the first can include a small amplification on any chromosome, and the second can exclude such.

The signal intensity produced by hybridization of the labeled test DNA can be compared to the signal intensity produced by hybridization of the labeled first reference DNA in the one or more pre-defined regions, to determine a first estimate of copy number, the signal intensity produced by hybridization of the labeled test DNA can be compared to the signal intensity produced by hybridization of the labeled second reference DNA in the one or more pre-defined regions, to determine a second estimate of copy number, and the first and second estimates of copy number can be combined to obtain an overall estimate of copy number. In some embodiments, the signal intensities are normalized before the copy number is estimated.

In some cases, the first reference genomic DNA from a reference sample, or an amplification product thereof, can comprise an amplification product produced by a first amplification technique, and the second reference genomic DNA from a reference sample, or an amplification product thereof, can comprise an amplification product produced by the same first amplification technique. The first reference genomic DNA from a reference sample, or an amplification product thereof, can comprise a plurality of different amplification products each formed by amplifying a different starting concentration of a same first reference genomic DNA. The method can comprise determining an aneuploidy status of a human polar body or embryo based on the copy number estimate. The method can further comprise using copy number information, for example, aneuploidy status, to select embryos for implantation in IVF procedures. The method can comprise isolating genomic DNA from the test sample to form the sample genomic DNA or amplification product thereof.

The test sample can comprise at least one cell from an embryo. The first genomic reference DNA can comprise DNA obtained from tissue or cells of an animal having a chromosomal anomaly. In some embodiments, the first genomic reference DNA comprises DNA obtained from mosaic tissue or cells. In some cases, the labeled first reference DNA has a first concentration of DNA and comprises normal male DNA, the labeled second reference DNA has a second concentration of DNA and comprises the same normal male DNA as the labeled first reference DNA, and the second concentration is diluted relative to the first concentration. Female DNA can be used instead of male DNA, or in addition to male DNA. The labeled first reference DNA can comprise pooled genomic DNA extracted from blood samples taken from at least two individuals.

According to the present teachings, a method for determining the presence of a copy number imbalance in genomic DNA of a test sample is provided, comprising labeling a test DNA to form labeled test DNA, hybridizing the labeled test DNA to a first hybridization array, analyzing the first hybridization array after the hybridizing to obtain first hybridization results, and comparing the first hybridization results with historical reference hybridization results from the hybridization of a labeled first reference DNA to a second hybridization array. The method can further comprise comparing the first hybridization results with historical reference hybridization results from the hybridization of a labeled second reference DNA to a third hybridization array, and determining the presence of a copy number imbalance by identifying one or more regions of the first hybridization array where the signal intensities differ from the signal intensities produced in one or more corresponding regions of at least one of the second hybridization array and the third hybridization array. The labeled first reference DNA can be from a male animal of a first species and the labeled second reference DNA can be from a female animal of the first species.

The present teachings also provide a library of reference array data sets stored in a processor. Each reference array data set can comprise data gathered from a respective reference array during a copy number hybridization assay carried out on the respective reference array, wherein (1) each reference array from which a respective data set is gathered, and includes elements which are common with each other reference array from which a data set is gathered and (2) each copy number hybridization assay, from which a respective data set is gathered, is carried out under one or more different conditions than each other copy number hybridization assay from which a data set is gathered. At least two reference array data sets of the library can differ from each other. In some embodiments, some of the reference sets are generated under identical conditions, to assess variability in the technique. Each reference array data set can comprise fluorescent signal intensity data.

The present teachings also provide a method comprising comparing a test array data set gathered from a test array during a copy number hybridization assay, to the reference array data sets of the library, and using a signal processor to determine a ratio between a test array data set and a data set from the library. A best fit data set can be determined from the library and can be the reference array data set determined by the processor to maximize the SNR of the ratio set so obtained.

According to the present teachings, a kit is also provided, and comprises a first copy number hybridization array, a second copy number hybridization array identical to the first copy number hybridization array, a third copy number hybridization array identical to the first copy number hybridization array, a first reference genomic DNA, a second reference genomic DNA, and instructions for comparing test results generated from a hybridization assay carried out on the first copy number hybridization array, to test results generated from a hybridization assay carried out on the second copy number hybridization array using the first reference genomic DNA. The instructions can also be for comparing test results generated from a hybridization assay carried out on the first copy number hybridization array, to test results generated from a hybridization assay carried out on the third copy number hybridization array using the second reference genomic DNA. In some cases, the first reference genomic DNA can comprise an amplification product of a reference genomic DNA. The present teachings also provide a kit comprising a copy number hybridization array, an electronic storage medium comprising a plurality of reference array data sets stored thereon, and instructions for comparing a data set corresponding to test results generated from a hybridization assay carried out on the copy number hybridization array, to the plurality of reference array data sets.

As the measurements of the test and reference DNA samples can occur in separate hybridization arrays, contrasting dyes for labeling are not necessary to carry out the detection method. Also, test DNA can be compared to an unlimited number of reference samples, rather than simply a co-hybridized reference. In this way as many comparisons as required can be performed in order to determine an optimal assay result for the test sample.

Use of more than one reference DNA can further avoid the risk of assay failure due to poor matching of test and reference DNA and permit selection of a single optimal pairing of test and reference DNA. The plurality of reference DNA can include reference DNA that is well-matched to test DNA obtained from DNA amplification of a single cell. In other words, a single reference DNA from the range of reference DNA generated can be selected that gives the best comparison to the test DNA. For example, reference DNA well-matched to test DNA can be achieved by generating a range of reference DNA samples through small modifications in the amplification protocol. Such small modification in the amplification protocol can lead to a spread of technical variation. In addition, the reference DNA that is generated can have specific known biological properties. For example, the reference DNA that is generated can be derived from a mosaic individual or from an individual of a particular sex. The reference DNA that is generated can have one or more chromosomal anomalies. The reference DNA can be derived from a compromised cell in order to match the condition of the test sample. The reference DNA can be derived from an individual biologically related to the test sample.

Hybridization array, as used herein, can comprise a microarray, or a collection of solid support-bound unlabeled target nucleic acids (probes), for example, an array of clones which have been mapped to chromosomal locations. The hybridization array can comprise a plurality of probes or target nucleic acid molecules, such as at least two target nucleic acid molecules, bound to a solid support or surface. The target nucleic acid molecules can be organized in predefined locations on the solid surface with discrete locations for each of the probes. The target nucleic acid molecules bound to the solid surface can be a plurality of the same target nucleic acid molecules, a plurality of different nucleic acid molecules, or a combination of the two. For example, in embodiments where it is desired to multiplex the detection assay (i.e., detect more than one nucleic acid molecule at a time), a plurality of different target nucleic acid molecules that bind to different nucleic acid molecules can be used. The solid surface can be any surface suitable for array CGH including both flexible and rigid surfaces. Flexible surfaces can include, but are not limited to, nylon membranes. Rigid surfaces can include, but are not limited to, glass slides. The solid surface can further comprise a three dimensional matrix or a plurality of beads. Any suitable method for immobilizing the target nucleic acids on the solid surface can be used.

It should be understood that while hybridization of DNA is described herein, any kind of nucleic acid, such as RNA, DNA, or cDNA, can be used. Similarly, the target nucleic acid molecules or probes can be, for example, RNA, DNA, or cDNA. The nucleic acids can be derived from any organism. The probes can be synthetic oligonucleotides or can be derived from cloned DNA or PCR products. The oligonucleotides can be synthesized in situ or synthesized and then arrayed ex situ. The cloned DNA can be bacterial artificial chromosome (BAC) clones or P1-derived artificial chromosomes (PAC). The sequence of the nucleic acid molecules can originate from a chromosomal location known to be associated with disease, can be selected to be representative of a chromosomal region whose association with disease is to be tested, or can correspond to genes whose transcription is to be assayed.

A reference DNA can be labeled and hybridized to a hybridization array. The hybridization array can be washed to remove any non-specifically bound labeled material. The hybridization array can then be scanned and the signal intensity of the reference DNA can be recorded and stored as historical reference hybridization results for subsequent comparison with test hybridizations results for a test DNA sample. Similarly, a set of historical reference hybridization results can be generated and recorded for a plurality of different reference DNA. The plurality of reference DNA samples can be labeled and hybridized individually to separate hybridization arrays having the same array design. The hybridization arrays can be scanned and the scanned data can be transformed into historical reference hybridization results, and stored for later use. Since the historical reference hybridization results can be recorded, hybridization of the plurality of reference DNA does not need to be done more than once. The historical reference hybridization results can be used repeatedly for subsequent assays using one or more different test DNA. The test DNA can be labeled and hybridized to a hybridization array having the same array design as the hybridization arrays used to obtain the historical reference hybridization results. The historical reference hybridization results can be transferred electronically or in an electronic storage medium to end users.

It should be understood that "scanning" as used herein, refers to any conventional method carried out by a scanner that would allow detection of hybridization of a sample to a hybridization array. Scanning can include, for example, emitting light from a light source of a the scanner and, at a detector of the scanner, receiving the emitted light that reflects off of a respective location of the hybridization array. In some embodiments, scanning can include, for example, exciting fluorescent dyes on a microarray, and at a detector of the scanner, measuring emitted fluorescent intensity. Scanning is further described for example, in WO 96/17958 and in U.S. patent application Ser. No. 12/609,156, filed Oct. 30, 2009, each of which is incorporated herein in its entirety by reference.

FIG. 1 is a flowchart depicting one method for determining copy number of a test DNA sample. As shown in FIG. 1, a labeled test DNA sample can be hybridized to hybridization area A. The signal intensity or amplitude generated by the hybridization can be measured to construct a test DNA sample amplitude profile. The test DNA sample amplitude profile can be normalized. A set of reference DNA samples can be selected and separately hybridized to hybridization areas other than hybridization area A. The signal intensity or amplitude generated by the hybridization of each reference DNA can be measured to construct a reference DNA amplitude profile. The reference DNA amplitude profile can be normalized. Copy number for the test DNA sample can be determined by comparing the test DNA sample amplitude profile to the reference DNA amplitude profile. In some embodiments, by identical array, what is meant is an array comprising a lot of the same content, for example, at least 90% of the same content but which can differ in other content. Similarly, slight variations in amplification procedure can also be used while still being considered identical.

In some embodiments, each reference DNA will have an associated amplitude profile. An initial estimate of copy number is then determined by taking the ratio of the test amplitude to the reference amplitude (or multiple reference amplitudes), and possibly various normalizations. There is naturally noise in this estimate of copy number, and a further step can be used to assess whether an estimated copy number is likely to correspond to a genuine change in biological copy number, or is simply due to noise (and therefore a copy number of zero).

The plurality of different reference DNA can comprise reference DNA that have specific known biological properties. For example, the reference DNA can be obtained from male or female samples. The reference DNA can be obtained from cell lines with a desired chromosomal anomaly. The reference DNA can be obtained from mosaic sample. Synthetic mosaic reference samples can be constructed by combining cells or extracted DNA with differing but known karyotypes so as to replicate mosaic karyotype patterns. This combining can occur at any stage during the preparation of reference DNA, or following labelling.

The reference DNA can be derived from a compromised cell in order to match the condition of the test sample. Reference DNA can be derived from individuals biologically related to the individual from whom the test sample was taken.

The test DNA can be prepared from a test sample, such as, a test cell, cell population, or tissue under study. The test DNA can be isolated from one or more test cells. The test DNA can be obtained from a polar body wherein half of an egg's chromosome complement is ejected prior to fertilization. The test DNA can be obtained from a blastomere, a single cell extracted from an eight cell embryo, or a small number of cells from a blastocyst or associated biopsy, for example, a trophoectodural biopsy. The test cell can comprise at least one cell from an embryo. DNA amplification procedures can be used in order to produce large numbers of copies of the test DNA.

The reference DNA can be prepared from a reference cell, cell population, or tissue. Reference cells can be normal non-diseased cells, or they can be from a sample of diseased tissue that serves as a standard for other aspects of the disease. The reference DNA is the genomic material for which the copy number of the genes or nucleic acid molecules of interest are already known.

The reference DNA can be generated using a variety of starting materials. Examples of starting materials can include tissue, such as blood, donated by one or more individuals. Other sources of starting materials can include single cells. Standard procedures can be used to isolate the reference DNA from appropriate tissues or cells. The reference DNA or starting material can be chosen from an individual having normal chromosomes and/or an individual having chromosomal anomalies, such as gain or loss of one or more chromosomes or alternatively gain or loss of one or more chromatid. The single cells can be derived from cell culture in vitro or can be ex vivo human cells, either of the same type as the intended test sample or of a different type. Single cells can be selected because they have a chromatin structure which is similar or dissimilar to that of the intended test sample, for example sperm cells with dense chromatin can be selected. Similarly cells can be chosen which are at differing stages of the cell cycle. Alternatively, high quality and concentrated genomic reference DNA can be extracted from cell culture or blood and can be diluted post-extraction to levels that are comparable to concentrations obtained from a single cell.

Although, a familial relationship between the donor of materials used to produce reference DNA and the test sample can be present, such a relationship is not required. Reference material can be obtained from one or both parents in order to be able to make direct comparisons between the test sample and parental samples.

A variety of conditions can be used to generate a plurality of reference DNA of differing quality. Reference DNA can be generated from cells of differing integrity, for example, reference samples generated from compromised cells. Reference DNA can be treated post-sample collection, such as DNA extracted from formalin-fixed paraffin-embedded tissue. The reference DNA can be subject to physical treatments, such as heating or sonication. Chemical treatments, such as, enzymatic digestion or proteinase digestion can also be used. Other treatments can be performed, which simulate test sample conditions during IVF procedures. Such treatments can include mineral oil contamination and contamination with culture media in order to normalize any contribution these factors make to differences in assay performance between test and reference samples.

The preparation of reference DNA can involve the application of whole genome amplification. The whole genome amplification protocol can be varied so as to introduce variations into the amplified DNA products. For amplification, a SUREPLEX DNA amplification, or other suitable amplification can used. The precise nature of the DNA amplification used is not critical to the teachings. While un-amplified genomic reference DNA can be used, high noise levels can result due to poor matching of amplified test DNA with un-amplified reference DNA. Thus, the reference material used can be a 'normal' pooled DNA sample diluted to contain a broadly similar quantity of DNA as a small number of single cells. This diluted reference material can then be amplified using the same method as the test sample. In order to compensate for differences between amplification of test and reference DNA, the set of reference samples can be carefully constructed so as to span the space of variations responsible for poor matching. This strategy can reduce the risk of assay failure due to poor matching of test and reference samples associated with conventional arrayCGH. Separating the measurement of test and reference samples, as described herein, allows comparison of measurements made on a single test sample with measurements made on a series of reference samples. In this way a single optimal pairing of test and reference samples can be found, or alternatively, results from multiple comparisons can be combined and compared to test DNA.

Figure 2:
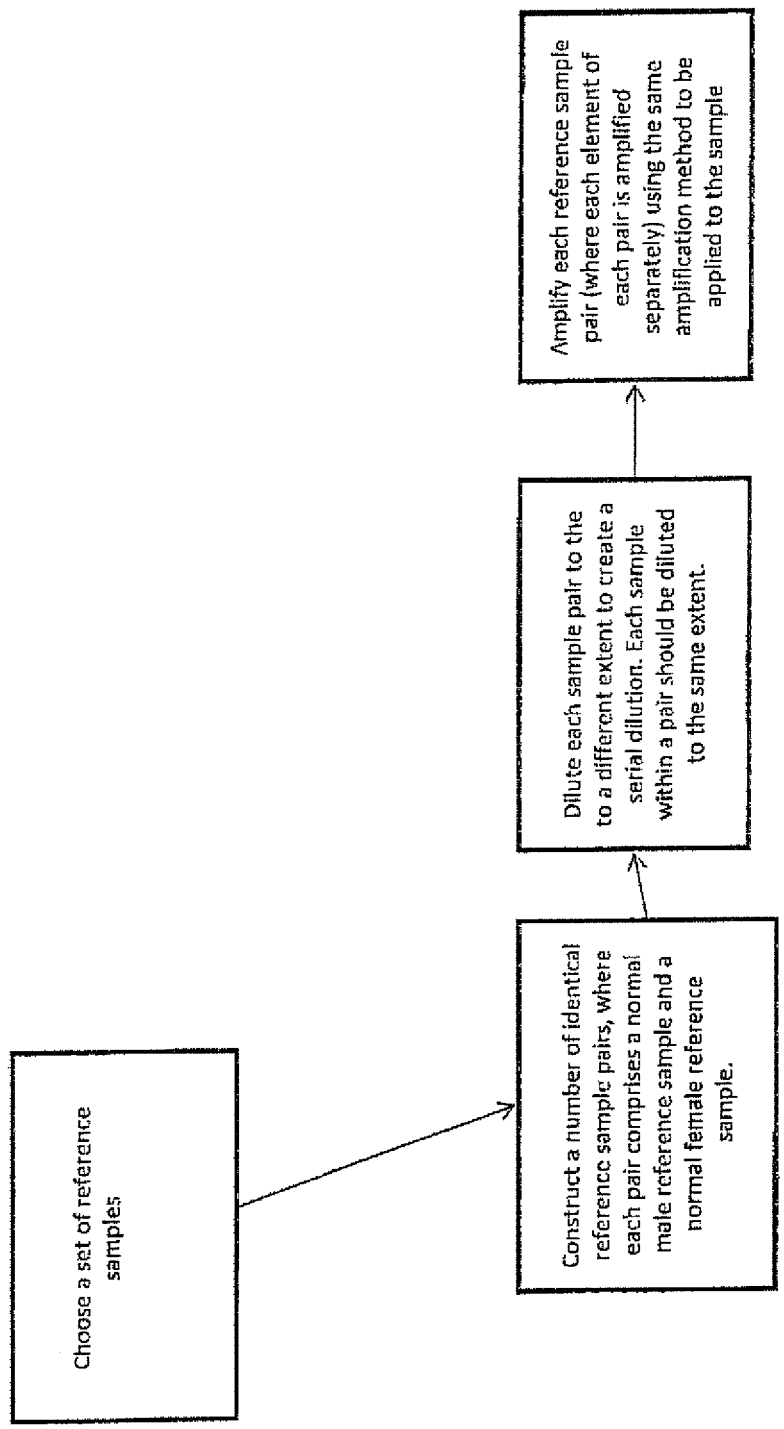
FIG. 2 is a flowchart showing an exemplary method for preparing a set of reference DNA samples, according to the present teachings.

FIG. 2 is a flowchart showing an exemplary method for preparing a set of reference DNA samples. As shown in FIG. 2, variations can be introduced to reference DNA by varying the amplification protocol that is used to create a set of reference DNA samples. A number of identical reference DNA sample pairs can be constructed. Each reference DNA sample pair can comprise a normal male reference DNA and a normal female reference DNA. Each sample pair can be diluted to a different extent to create a serial dilution. Each reference DNA with a pair can be diluted to the same extent. Each reference DNA of each sample pair can be amplified separately using an amplification method that is the same as that used to amplify a test DNA.

The test DNA and the reference DNA can be labeled to allow detection of hybridization complexes. The particular label attached to the DNA is not a critical aspect of the teachings, as long as the label does not significantly interfere with the hybridization of the DNA to the target nucleic acid molecules. The label can be any material having a detectable physical or chemical property. The label can include, for example, a fluorescent dye, a radiolabel, or an enzyme. Generally, fluorescent labels commonly used for arrayCGH, such as Cy3 and Cy5, are preferred. A CYTOCHIP labeling kit from BLUEGNOME, for example, can be used. Standard methods for detection and analysis of signals generated by the labels can be used. For fluorescent labels, standard methods generally used in array comparative genomic hybridization ("arrayCGH") can be used. The hybridization arrays can be imaged in a fluorescence microscope with a polychromatic beam-splitter. The different color images can be acquired with a CCD camera, a laser scanner, a combination thereof, and the like, and the digitized images can be stored in a computer. A computer program can then be used to analyze the signals produced by the array.

The selection of a single optimal pairing of test and reference DNA and determination of a copy number imbalance in test DNA can be automated to simplify data analysis and interpretation and/or increase reproducibility. A set of algorithms can be provided which automate the choice of reference data as well as scoring of the assay. These algorithms can simplify data analysis, interpretation, and/or increase reproducibility. The algorithms can comprise a reference selection algorithm and a calling algorithm. The reference selection algorithm can compare the test hybridization results for a test DNA with a set of corresponding historical reference hybridization results and determine which reference DNA of the plurality of reference DNA yields the best comparison to the test DNA.

In the event that the detection method can suffer from spatial noise due to inter array hybridization variability and/or hybridizing samples on different days. As such, the detection method can comprise methods for spatial bias correction or methods to spatially correct for inter-array hybridization. Any spatial bias which may exist due to differences in hybridization of the test DNA and the reference DNA can be detected and removed by methods known in the art, for example, as described in U.S. patent application Ser. No. 12/609,156, filed Oct. 30, 2009, the contents of which are incorporated by reference herein in their entireties.

The reference selection algorithm can characterize the results of each test/reference comparison with a performance metric. The performance metric can be, for example, signal to noise ratio. The signal component can be defined as the difference between the medians of the $\log_2$ ratios of a chosen chromosome pair of the hybridization array where ratios are between test and reference. The noise component can be obtained by taking the set of target nucleic acids or probes in the hybridization array for each chromosome and subtracting the chromosome median $\log_2$ ratio from each individual probe $\log_2$ ratio. Once the chromosome trends are removed, the noise can be determined by calculating the inter quartile range over all probes.

The reference selection algorithm can select the reference DNA that maximizes the SNR of the ratiometric data, indicative of copy number in the test DNA. The test-reference pairing can then be automatically presented to the calling algorithm. The calling algorithm can be applied to identify regions of copy number imbalance between the test and reference samples. The calling algorithm can compare the observed pattern of imbalance to the expected pattern of imbalance. Because the karyotype of the reference sample is known, the karyotype of the test sample can then be inferred. A final classification of the sample can be either "euploid" (no copy number imbalance) or "aneuploid" (copy number imbalance). In some cases, the test data can be of poor quality, such that any results obtained would be unreliable. In these circumstances, the calling algorithm may classify the result as "no result."

Figure 3:
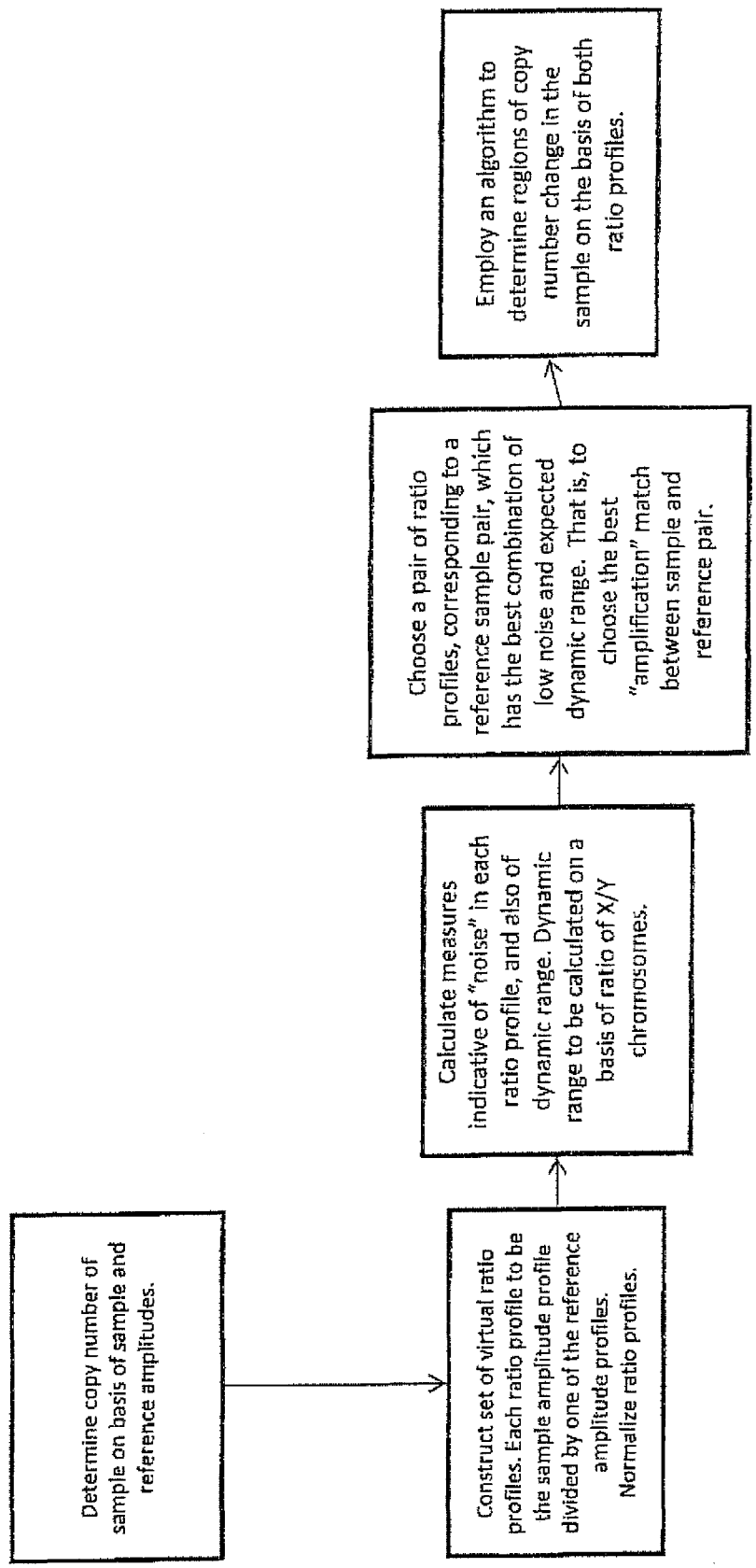
FIG. 3 is a flowchart showing how copy number of a test DNA sample can be determined, according to the present teachings.

FIG. 3 is a flowchart showing how copy number of a test DNA sample can be determined. As shown in FIG. 3, a set of virtual ratio profiles can be constructed by dividing a test DNA sample amplitude profile by the reference DNA amplitude profile of each reference DNA. The "noise" and "dynamic range" of each virtual ratio profile can be calculated. The dynamic range can be calculated on a basis of ratio of X/Y chromosomes. A pair of ratio profiles can be selected, corresponding to a reference sample pair, which has the best combination of low noise and expected dynamic range. In other words, the best "amplification" match of test DNA and reference DNA pair can be selected. The calling algorithm can be employed to determine regions of copy number change in the test DNA based on the pair of ratio profiles.

It should be understood that if the test sample from which the test DNA is isolated is from a first polar body, one optimal pairing of reference DNA and test DNA can be made although it may still be desirable to select the second for reasons elsewhere outlined. If the test DNA is isolated from a blastomere biopsy for which the gender of the sample is not known in advance, the reference selection algorithm can select two optimal pairings. In some embodiments, an unlimited number of pairings can be chosen. If the test DNA is isolated from a blastomere biopsy, the reference DNA can comprise male genomic DNA and female genomic DNA of varying quality. The two optimal pairings can comprise a test DNA with a male reference DNA and the test DNA with a female reference DNA. The calling algorithm can then identify copy number imbalances present in one or both of the pairings. These imbalances can be compared to the expected pattern of imbalances. Because the karyotypes of both reference samples are known, the karyotype of the test sample can then be inferred.

Figure 4:
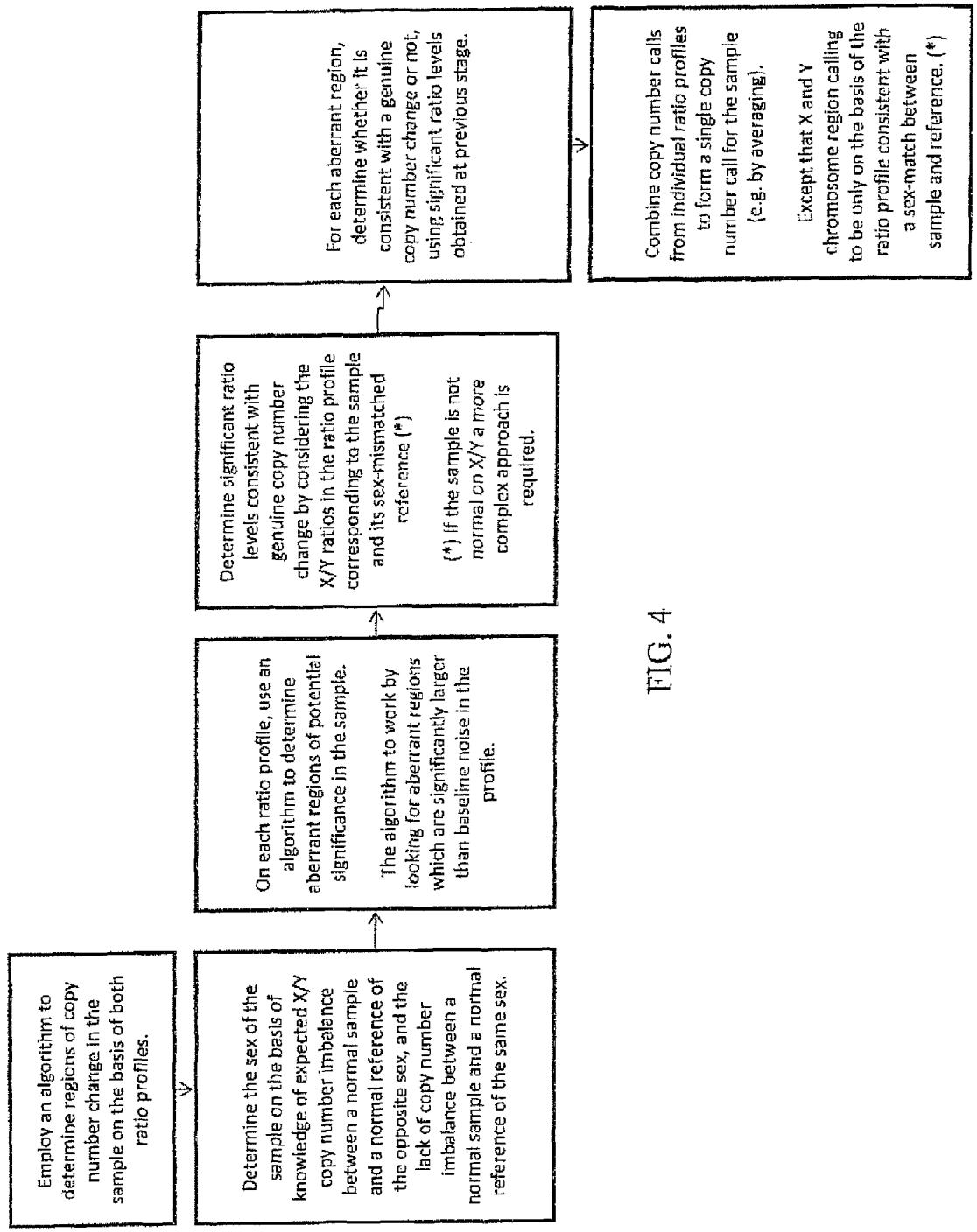
FIG. 4 is a flowchart showing how regions of copy number change in a test DNA sample can be determined based on two ratio profiles, according to the present teachings.

FIG. 4 is a flowchart showing how regions of copy number change in a test DNA sample on the basis of two ratio profiles can be determined. As shown in FIG. 4, the signal intensity after hybridization of a normal test DNA sample can be compared to the signal intensity of the normal male and female reference DNA to determine a copy number imbalance. The test DNA sample can be the same sex of the reference DNA that has the same copy number as the test DNA. Ratio profiles of a normal test DNA and a normal male reference DNA as well as the test DNA and a normal female reference DNA can be obtained. For each ratio profile, an algorithm can be used to determine aberrant regions of potential significance in the test DNA, in other words, aberrant regions which are significantly larger than baseline noise in the profile. Significant ratio levels consistent with genuine copy number change can be determined by considering the X/Y ratios in the ratio profile corresponding to the test DNA sample and its sex-mismatched reference DNA. A determination can be made whether each aberrant region is consistent with a genuine copy number change or not, using significant ratio levels obtained at previous stages. Copy number calls from individual ratio profiles can be combined to form a single copy number call for the test DNA, for example, by averaging. It should be understood, however, that X and Y chromosome region calling can preferentially be on the basis of the ratio profile consistent with a sex-match between sample and reference.

More than one test DNA can be hybridized to the same hybridization area. For example, two or more test DNA samples can be labeled with different dyes and hybridized to the same hybridization area.

In some embodiments, the test sample is male, the first reference is female, and the second reference is male. In some cases, the test sample is female, the first reference is male, and the second reference is female. In either case, the first reference can be used to establish a dynamic range which can be used to detect all the chromosomes, and the second reference can be used for calling on X/Y. To address challenges produced by not knowing the sex of the sample, if the test sample is a polar body a female reference and a male reference can both be used such that one reference is matched to the sample and the other provides dynamic range information.

It is to be understood that "copy number" as used herein is relative to a reference genome. For example, if a reference is a mixture of male DNA and female DNA, copy number is not necessarily an integer. In some cases a triploid reference can be used as a normal and would have yet a different copy number.

According to the present teachings, a first reference is an amplification product of a sample including a copy number change in a first determined reference. In some embodiments, a first reference is an amplification product of a first predetermined region and a second reference has a deletion in the predetermined region rather than no change in the predetermined region.

According to the present teachings, first, second, third, and any other hybridization areas can be the same if different labels are used.

While the methods described herein are designed for IVF, the methods can also be applicable in a prenatal, oncology, and/or stem cell context. The detection method further allows a multitude of references representing different degrees of mosaicism, under different amplification conditions to be used.

Even where the sex of the sample is known, it is still generally useful to be able to run the sample against both a sex matched and sex mismatched references. For example, in the case of testing a polar body, it can be known that the sample is female and therefore a male reference is the defacto choice for reference in order to get an internal dynamic range control: However, this can have the side effect of complicating interpretation of the X and Y chromosomes of the polar body. It is therefore still an advantage wherein the sex mismatch is used to calculate dynamic range and provide calls on chromosomes 1-22, and the sex match is used to call all chromosomes.

In some cases, in predefined regions, at least one reference sample has copy number difference with the test sample. This copy number difference can be used as a "control" to effectively indicate the dynamic range of the experiment (which is dependent on the individual test sample, and hybridization conditions, in question). For example, if a copy number difference of "1" is expected between the test and a particular predefined region in a reference, and due to experimental reasons, the difference is only "0.25," information is gained about the dynamic range of the experiment such that 0.25 can be significant in a particular experiment. This estimate of dynamic range, or significance," can then be used to assess copy number changes in other reference datasets, or different chromosomes on the same reference dataset.

EXAMPLES

Figure 5:
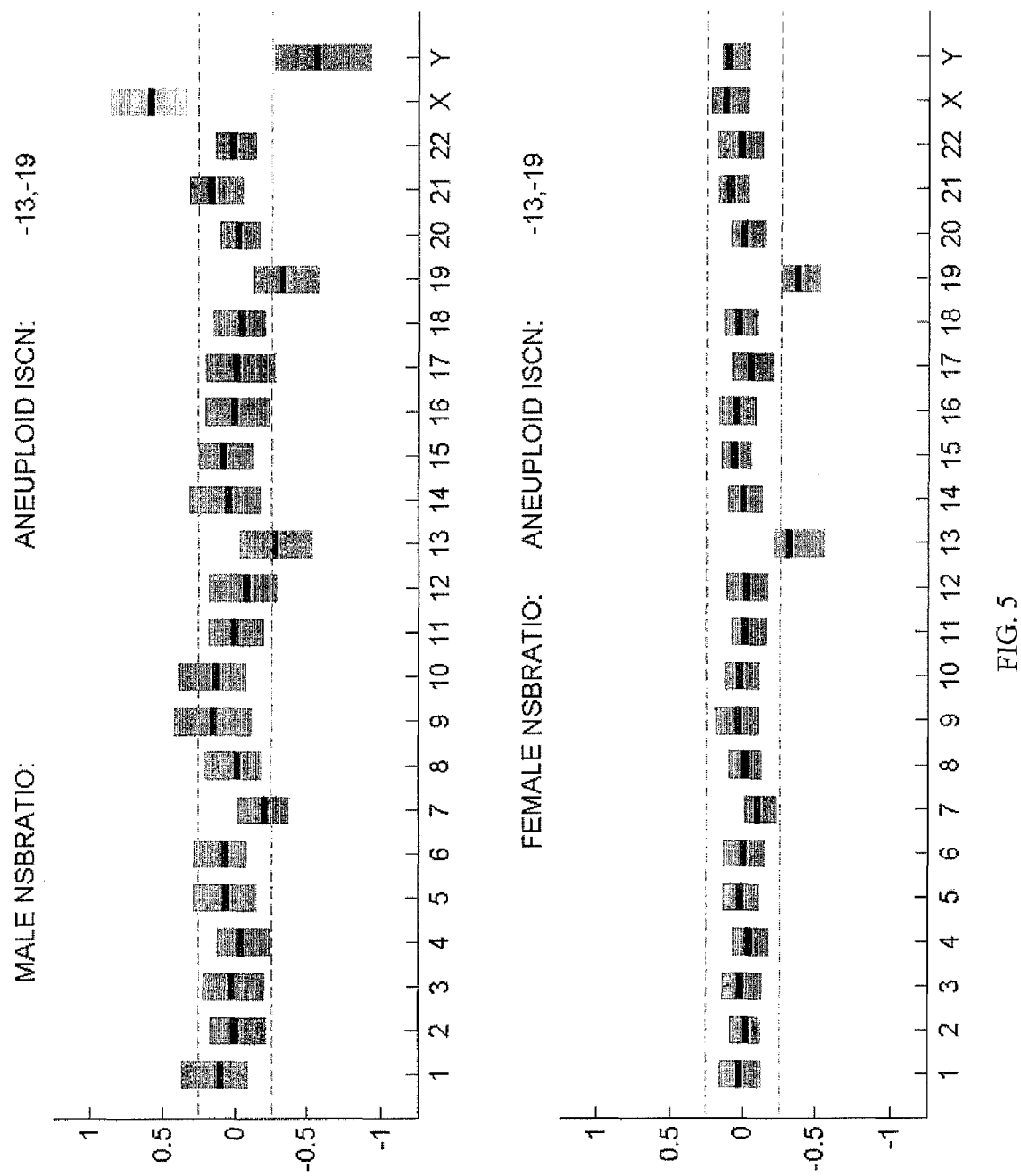
FIG. 5 shows a pair of plots wherein the top plot shows a sample compared to a male reference and the bottom plot shows a sample compared to a female reference.

A sample comprising a normal female missing 1 copy of chromosomes 13 and 19 was provided. FIG. 5 shows a pair of plots wherein the top plot of each shows a sample compared to a male reference and the bottom plot of each shows a sample compared to a female reference. In the top plot of FIG. 5, the sample is compared with a male reference and the X chromosome shows as a gain because there are two copies of X in the female and only one in the male reference, and similarly the Y chromosome appears as a loss as there is no Y in the female and one in the male reference. These expected X/Y changes provide an indication of what is significant. Chromosomes 13 and 19 are clear losses.

The bottom plot in FIG. 5 shows the same sample compared with a female reference. In this case, the number of X and Y chromosomes is expected to be the same in both sample and reference. Once again, the losses on chromosome 13 and 19 are visible, particularly when combined with the information about dynamic range obtained from the X/Y comparisons in the top plot.

The entire contents of all cited references in this disclosure are incorporated herein in their entireties by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the teachings be limited to the specific values recited when defining a range.

Other embodiments of the present teachings will be apparent to those skilled in the art from consideration of the present specification and practice of the present teachings disclosed herein. It is intended that the present specification and examples be considered as exemplary only with a true scope and spirit of the teachings being indicated by the following claims and equivalents thereof.

What is claimed is:

1. A method for screening a preimplantation human embryo for implantation, the method comprising:
  a) labeling a first sample genomic DNA from a first test sample obtained from a preimplantation human embryo, or an amplification product thereof, thereby forming a labeled first test DNA, the preimplantation human embryo having been generated by in-vitro fertilization, the first sample genomic DNA comprising DNA sequences from a plurality of different human chromosomes, said first sample genomic DNA or said amplification product thereof being labeled by attaching labels that are capable of producing detectable signals to a plurality of different DNA sequences from one or more human chromosomes in the first sample genomic DNA;
  b) hybridizing the labeled first test DNA to a first hybridization array that is configured to hybridize to a plurality of different DNA sequences from X and Y chromosomes and a specific human chromosome at different respective predefined locations of the first hybridization array;
  c) labeling a first reference genomic DNA from a first reference sample obtained from a male human having two copies of the specific human chromosome, or an amplification product thereof, thereby forming a labeled first reference DNA, said first reference genomic DNA or said amplification product thereof being labeled by attaching the labels to a plurality of different DNA sequences from one or more human chromosomes in the first reference genomic DNA;
  d) hybridizing the labeled first reference DNA to a second hybridization array that is identical to the first hybridization array and that is configured to enable a copy number estimate of the number of copies of the specific human chromosome in the first sample genomic DNA based on a comparison of scanning results from scanning the different respective predefined locations of the first hybridization array to scanning results from scanning the corresponding different respective predefined locations of the second hybridization array;
  e) labeling a second reference genomic DNA from a second reference sample obtained from a female human having two copies of the specific human chromosome, or an amplification product thereof, thereby forming a labeled second reference DNA, said second reference genomic DNA or said amplification product thereof being labeled by attaching the labels to a plurality of different DNA sequences from one or more human chromosomes in the second reference genomic DNA;
  f) hybridizing the labeled second reference DNA to a third hybridization array that is identical to the first hybridization array and that is configured to enable a copy number estimate of the number of copies of the specific human chromosome in the first sample genomic DNA based on a comparison of scanning results from scanning the different respective predefined locations of the first hybridization array to scanning results from scanning the corresponding different respective predefined locations of the third hybridization array;
  g) scanning the first hybridization array after the hybridization of the labeled first test DNA to the first hybridization array and determining signal intensities produced by the hybridization of the labeled first test DNA to the first hybridization array at the different respective predefined locations of the first hybridization array;
  h) scanning the second hybridization array after the hybridization of the labeled first reference DNA to the second hybridization array and determining signal intensities produced by the hybridization of the labeled first reference DNA to the second hybridization array at the corresponding different respective predefined locations of the second hybridization array;
  i) scanning the third hybridization array after the hybridization of the labeled second reference DNA to the third hybridization array and determining signal intensities produced by the hybridization of the labeled second reference DNA to the third hybridization array at the corresponding different respective predefined locations of the third hybridization array;
  J) determining the sex of the preimplantation human embryo by comparing the signal intensities at the different respective predefined locations of the first hybridization array with the signal intensities at the corresponding different respective predefined locations of the second hybridization array and the third hybridization array;
k) selecting a sex-matched hybridization array from the second hybridization array and the third hybridization array by determining, based on results obtained from step j), which one of the first reference genomic DNA and the second reference genomic DNA is sex-matched with the first sample genomic DNA;
l) estimating a copy number of the specific human chromosome in the first sample genomic DNA by comparing the signal intensities at the different respective predefined locations of the first hybridization array to the signal intensities at the corresponding different respective predefined locations of at least the sex-matched hybridization array;
m) determining the presence or absence of a copy number imbalance of the specific human chromosome in the first sample genomic DNA of the first test sample based on results obtained in step l); and
n) screening the preimplantation human embryo for implantation based on results obtained from step m).

2. The method of claim 1, wherein the signal intensities produced by hybridization of the labeled first test DNA in the different respective predefined locations of the first hybridization array is compared to the signal intensities produced by the hybridization of the labeled first reference DNA in the corresponding different respective predefined locations of the second hybridization array, thereby obtaining a first estimate of the copy number, the signal intensities produced by the hybridization of the labeled first test DNA in the different respective predefined locations of the first hybridization array is compared to the signal intensities produced by the hybridization of the labeled second reference DNA in the corresponding different respective predefined locations of the third hybridization array, thereby obtaining a second estimate of the copy number, and the first estimate and the second estimate of the copy number are combined to obtain an overall estimate of the copy number.

3. The method of claim 1, wherein the signal intensities from the first array, the second array and the third array are normalized before the copy number is estimated.

4. The method of claim 1, wherein the first reference genomic DNA from the first reference sample, or an amplification product thereof, comprises an amplification product produced by an amplification technique, and the second reference genomic DNA from the second reference sample, or an amplification product thereof, comprises an amplification product produced by said amplification technique.

5. The method of claim 1, wherein the first reference genomic DNA from the first reference sample, or an amplification product thereof, comprises a plurality of different reference DNAs at different respective concentrations.

6. The method of claim 1, further comprising:
hybridizing a labeled third reference DNA to a fourth hybridization array that is identical to the first hybridization array and that is configured to enable a copy number estimate of the number of copies of the specific human chromosome in the first sample genomic DNA based on a comparison of the scanning results from scanning the different respective predefined locations of the first hybridization array to scanning results from scanning the corresponding different respective predefined locations of the fourth hybridization array;
hybridizing a labeled fourth reference DNA to a fifth hybridization array that is identical to the first hybridization array and that is configured to enable a copy number estimate of the number of copies of the specific human chromosome in the first sample genomic DNA based on a comparison of the scanning results from scanning the different respective predefined locations of the first hybridization array to scanning results from scanning the corresponding different respective predefined locations of the fifth hybridization array; and
hybridizing a labeled fifth reference DNA to a sixth hybridization array that is identical to the first hybridization array and that is configured to enable a copy number estimate of the number of copies of the specific human chromosome in the first sample genomic DNA based on a comparison of the scanning results from scanning the different respective predefined locations of the first hybridization array to scanning results from scanning the corresponding different respective predefined locations of the sixth hybridization array;
wherein each of the labeled third reference DNA, the labeled fourth reference DNA, and the labeled fifth reference DNA contains the labels that are capable of producing detectable signals and said estimating the copy number of the specific human chromosome in the first sample genomic DNA further comprises comparing the signal intensities of the first hybridization array to signal intensities generated by the hybridization of the labeled third reference DNA to the fourth hybridization array, the hybridization of the labeled fourth reference DNA to the fifth hybridization array, and the hybridization of the labeled fifth reference DNA to the sixth hybridization array at each of the corresponding different respective predefined locations of the fourth hybridization array, the fifth hybridization array and the sixth hybridization array.

7. The method of claim 1, wherein said determining the presence or absence of a copy number imbalance in step m) comprises determining an aneuploidy status of the embryo.

8. The method of claim 7, further comprising determining the suitability of the embryo for implantation in an in vitro fertilization procedure based on the aneuploidy status of the embryo.

9. The method of claim 1, further comprising isolating genomic DNA from the first test sample and forming the first sample genomic DNA or an amplification product thereof.

10. The method of claim 1, wherein the first test sample comprises at least one cell from a blastomere biopsy sample obtained from the preimplantation human embryo, a trophoectoderm biopsy sample obtained from the preimplantation human embryo, a blastocyst biopsy sample obtained from the preimplantation human embryo, or at least one cell extracted from an eight cell embryo.

11. The method of claim 1, wherein at least one of the first reference genomic DNA and the second reference genomic DNA comprises DNA obtained from tissue or cells of a human having a chromosomal anomaly.

12. The method of claim 1, wherein at least one of the first reference genomic DNA and the second reference genomic DNA comprises DNA obtained from mosaic tissue or cells.

13. The method of claim 1, wherein at least one of the first reference genomic DNA and the second reference genomic DNA comprises pooled genomic DNA extracted from blood samples taken from at least two humans.

14. A method for screening a preimplantation human embryo for implantation, the method comprising:
a) labeling a first sample genomic DNA from a first embryonic test sample obtained from a preimplantation human embryo, or an amplification product thereof, thereby forming a labeled first test DNA, the preimplantation human embryo having been generated by in-vitro fertilization, the first sample genomic DNA comprising DNA sequences from a plurality of different human chromosomes, said first sample genomic DNA or said amplification product thereof being labeled by attaching labels that are capable of producing detectable signals to a plurality of different DNA sequences from one or more human chromosomes in the first sample genomic DNA;

b) hybridizing the labeled first test DNA to a first hybridization array that is configured to hybridize to a plurality of different DNA sequences from X and Y chromosomes and a specific human chromosome at different respective predefined locations of the first hybridization array;

c) scanning the first hybridization array after the hybridizing step and determining signal intensities produced by the hybridization of the labeled first test DNA to a first hybridization array at the different respective predefined locations of the first hybridization array, thereby obtaining first hybridization array signal intensity results;

d) comparing the first hybridization array signal intensity results with first reference data comprising historical reference hybridization array signal intensity results from the hybridization of a labeled first reference DNA from a male human having two copies of the specific human chromosome to a second hybridization array that is identical to the first hybridization array and that is configured to enable a copy number estimate of the number of copies of the specific human chromosome in the first sample genomic DNA based on a comparison of the first hybridization array signal intensity results to the first reference data;

e) comparing the first hybridization array signal intensity results with second reference data comprising historical reference hybridization array signal intensity results from the hybridization of a labeled second reference DNA from a female human having two copies of the specific human chromosome to a third hybridization array that is identical to the first hybridization array and that is configured to enable a copy number estimate of the number of copies of the specific human chromosome in the first sample genomic DNA based on a comparison of the first hybridization array signal intensity results to the second reference data;

f) determining the sex of the preimplantation human embryo by comparing the first hybridization array signal intensity results with each of the first reference data and the second reference data;

g) selecting a sex-matched data from the first reference data and the second reference data by determining, based on results obtained from step f), which one of the first reference data and the second reference data is sex-matched with the first sample genomic DNA;

h) estimating a copy number of the specific human chromosome in the first sample genomic DNA by comparing the first hybridization array signal intensity results with the sex-matched data and determining the presence or absence of a copy number imbalance of the specific human chromosome in the first sample genomic DNA based on the copy number of the specific human chromosome in the first sample genomic DNA, and the sex-matched data; and i) screening the preimplantation human embryo for implantation based on results obtained from step h).

15. The method of claim 14, wherein at least one of the labeled first reference DNA and the labeled second reference DNA includes at least one copy number change in the specific human chromosome, relative to the labeled first test DNA.

16. The method of claim 15, wherein the labeled first test DNA and the labeled first reference DNA have the same copy number change in the specific human chromosome, and the labeled first test DNA and the labeled second reference DNA do not have the same copy number change in the specific human chromosome.

17. The method of claim 14, wherein said determining the presence or absence of a copy number imbalance in step h) comprises determining an aneuploidy status of the embryo.

18. The method of claim 17, further comprising determining the suitability of the embryo for implantation in an in vitro fertilization procedure based on the aneuploidy status of the embryo.

19. A method for screening a preimplantation human embryo for implantation, the method comprising:
  a) labeling a first sample genomic DNA from a first embryonic test sample obtained from a preimplantation human embryo, or an amplification product thereof, thereby forming labeled first test DNA, the preimplantation human embryo having been generated by in-vitro fertilization, the first sample genomic DNA comprising DNA sequences from a plurality of different human chromosomes, said first sample genomic DNA or said amplification product thereof being labeled by attaching labels that are capable of producing detectable signals to a plurality of different DNA sequences from one or more human chromosomes in the first sample genomic DNA;
  b) hybridizing the labeled first test DNA to a first hybridization array that is configured to hybridize to a plurality of different DNA sequences from a specific human chromosome at different respective predefined locations of the first hybridization array;
  c) labeling a first reference genomic DNA from a first reference sample obtained from a human having two copies of the specific human chromosome, or an amplification product thereof, thereby forming a labeled first reference DNA, said first reference genomic DNA or said amplification product thereof being labeled by attaching the labels to a plurality of different DNA sequences from one or more human chromosomes in the first reference genomic DNA;
  d) hybridizing the labeled first reference DNA to a second hybridization array that is identical to the first hybridization array and that is configured to enable a copy number estimate of the number of copies of the specific human chromosome in the first sample genomic DNA based on a comparison of scanning results from scanning the different respective predefined locations of the first hybridization array to scanning results from scanning the corresponding different respective predefined locations of the second hybridization array;
  e) labeling a second reference genomic DNA from a second reference sample obtained from a human having a known chromosomal anomaly in the form of a gain or loss of the specific human chromosome, or an amplification product thereof, thereby forming a labeled second reference DNA, said second reference genomic DNA or said amplification product thereof being labeled by attaching the labels to a plurality of different DNA sequences from one or more human chromosomes in the second reference genomic DNA;

f) hybridizing the labeled second reference DNA to a third hybridization array that is identical to the first hybridization array and that is configured to enable a copy number estimate of the number of copies of the specific human chromosome in the first sample genomic DNA based on a comparison of scanning results from scanning the different respective predefined locations of the first hybridization array to scanning results from scanning the corresponding different respective predefined locations of the third hybridization array;

g) scanning the first hybridization array after the hybridization of the labeled first test DNA to the first hybridization array and determining signal intensities produced by the hybridization of the labeled first test DNA to the first hybridization array at the different respective predefined locations of the first hybridization array;

h) scanning the second hybridization array after the hybridization of the labeled first reference DNA to the first hybridization array and determining signal intensities produced by the hybridization of the labeled first reference DNA to the second hybridization array at the corresponding different respective predefined locations of the second hybridization array;

i) scanning the third hybridization array after the hybridization of the labeled second reference DNA to the third hybridization array and determining signal intensities produced by the hybridization of the labeled second reference DNA to the third hybridization array at the corresponding different respective predefined locations of the third hybridization array;

j) comparing the signal intensities at the different respective predefined locations of the first hybridization array to the signal intensities at the corresponding different respective predefined locations of the second hybridization array;

k) comparing the signal intensities at the different respective predefined locations of the first hybridization array to the signal intensities at the corresponding different respective predefined locations of the third hybridization array;

l) selecting an optimal pairing of signal intensities from the signal intensities at the different respective predefined locations of the first hybridization array and from the signal intensities at the corresponding different respective predefined locations of the second hybridization array or the third hybridization array;

m) estimating a copy number of the specific human chromosome in the first sample genomic DNA by comparing the signal intensities of the optimal pairing of signal intensities;

n) determining the presence or absence of a copy number imbalance of the specific human chromosome in the first sample genomic DNA of the first test sample based on results obtained from step m); and o) screening the preimplantation human embryo for implantation based on results obtained from step n).

20. The method of claim 19, wherein the labeled first reference DNA has a first concentration of DNA and comprises an amplification product of a first concentration of a first DNA, and the labeled second reference DNA comprises an amplification product of the first DNA produced after diluting the first concentration of the first reference DNA.

21. A method for screening a preimplantation human embryo for implantation, the method comprising:

a) labeling a first sample genomic DNA from a first embryonic test sample obtained from a preimplantation human embryo, or an amplification product thereof, thereby forming a labeled first test DNA, the preimplantation human embryo having been generated by in-vitro fertilization, said first sample genomic DNA comprising DNA sequences from human chromosomes 13 and 19, said first sample genomic DNA or said amplification product thereof being labeled by attaching labels that are capable of producing detectable signals to a plurality of different DNA sequences from human X and Y chromosomes, to a plurality of different DNA sequences from human chromosome 13, and to a plurality of different DNA sequences from human chromosome 19;

b) hybridizing the labeled first test DNA to a first hybridization array, the first hybridization array configured to hybridize labeled DNA sequences from human X and Y chromosomes and from each of chromosomes 13 and 19 at different respective predefined locations of the first hybridization array;

c) labeling a first normal male reference genomic DNA from a first reference sample obtained from a male reference human, or an amplification product thereof, thereby forming a labeled first reference DNA, the male reference human having two copies of each of chromosomes 13 and 19, said first reference genomic DNA or said amplification product thereof being labeled by attaching the labels to DNA sequences from X chromosome, from Y chromosome, and from chromosomes 13 and 19 in the first normal male reference genomic DNA;

d) hybridizing the labeled first reference DNA to a second hybridization array that is identical to the first hybridization array and that is configured to enable a copy number estimate of the number of copies of each of human X chromosome, human Y chromosome, and chromosomes 13 and 19 in the first sample genomic DNA based on a comparison of scanning results from scanning the different respective predefined locations of the first hybridization array to scanning results from scanning the corresponding different respective predefined locations of the second hybridization array;

e) labeling a second normal female reference genomic DNA from a second reference sample obtained from a female reference human, or an amplification product thereof, and forming a labeled second reference DNA, the female reference human having two copies of each of chromosomes 13 and 19, said second reference genomic DNA or said amplification product thereof being labeled by attaching the labels to DNA sequences from X chromosome and from chromosomes 13 and 19 in the second normal female reference genomic DNA;

f) hybridizing the labeled second reference DNA to a third hybridization array that is identical to the first hybridization array and that is configured to enable a copy number estimate of the number of copies of each of X chromosome and chromosomes 13 and 19 in the first sample genomic DNA based on a comparison of scanning results from scanning the different respective predefined locations of the first hybridization array to scanning results from scanning the corresponding different respective predefined locations of the third hybridization array;

g) scanning the first hybridization array after the hybridization of the labeled first test DNA to the first hybridization array and determining signal intensities produced by the hybridization of the labeled first test DNA to the first hybridization array at the different respective predefined locations of the first hybridization array;

h) scanning the second hybridization array after the hybridization of the labeled first reference DNA to the second hybridization array and determining signal intensities produced by the hybridization of the labeled first reference DNA to the second hybridization array at the corresponding different respective predefined locations of the second hybridization array;

i) scanning the third hybridization array after the hybridization of the labeled second reference DNA to the third hybridization array and determining signal intensities produced by the hybridization of the labeled second reference DNA to the third hybridization array at the corresponding different respective predefined locations of the third hybridization array;

j) determining the sex of the preimplantation human embryo by comparing the signal intensities at the different respective predefined locations of the first hybridization array with the signal intensities at the corresponding different respective predefined locations of each of the second hybridization array and the third hybridization array;

k) selecting a sex-matched hybridization array from the second hybridization array and the third hybridization array by determining, based on results obtained from step j), which one of the first reference genomic DNA and the second reference genomic DNA is sex-matched with the first sample genomic DNA;

l) estimating a copy number of each of chromosomes 13 and 19 in the first sample genomic DNA by comparing the signal intensities at the different respective predefined locations of the first hybridization array to the signal intensities at the corresponding different respective predefined locations of at least the sex-matched hybridization array;

m) determining the presence or absence of a copy number imbalance for each of chromosomes 13 and 19 in the first sample genomic DNA of the first embryonic test sample, based on results obtained from step l); and n) screening the preimplantation human embryo for implantation based on results obtained from step m).

22. The method of claim 21, wherein the first sample genomic DNA is from a female human.

23. The method of claim 21, wherein the first sample genomic DNA is from a female human that lacks one copy of each of chromosomes 13 and 19.

* * * * *